US010962500B2

(12) United States Patent
Najar

(10) Patent No.: US 10,962,500 B2
(45) Date of Patent: Mar. 30, 2021

(54) NITRIDE BASED SENSOR

(71) Applicant: UNITED ARAB EMIRATES UNIVERSITY, Al Ain (AE)

(72) Inventor: Adel Najar, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 16/938,376

(22) Filed: Jul. 24, 2020

(65) Prior Publication Data
US 2020/0386709 A1 Dec. 10, 2020

Related U.S. Application Data

(62) Division of application No. 16/142,671, filed on Sep. 26, 2018, now Pat. No. 10,761,049.

(51) Int. Cl.
G01N 27/414 (2006.01)
G01N 33/00 (2006.01)
(52) U.S. Cl.
CPC ......... G01N 27/414 (2013.01); G01N 33/005 (2013.01)
(58) Field of Classification Search
None
See application file for complete search history.

(56) References Cited

U.S. PATENT DOCUMENTS

| 2011/0235031 A1* | 9/2011 | Dziecielewski ..... G01N 21/658 356/243.4 |
| 2014/0311905 A1 | 10/2014 | Stetter |
| 2016/0027656 A1* | 1/2016 | El Afandy ........ H01L 21/02002 257/76 |
| 2017/0038326 A1* | 2/2017 | Motayed .............. G01N 33/004 |
| 2017/0162896 A1* | 6/2017 | Pozvonkov ......... H01M 8/2428 |
| 2019/0214531 A1* | 7/2019 | Ng .......................... C25B 1/003 |

FOREIGN PATENT DOCUMENTS

WO 2018020422 A1 2/2018
WO WO-2018020422 A1 * 2/2018 ............. C25B 1/003

* cited by examiner

Primary Examiner — Paul M. West
Assistant Examiner — Mark A Shabman
(74) Attorney, Agent, or Firm — Hayes Soloway PC

(57) ABSTRACT

The present invention discloses a nitride based sensor including a nitride based semiconductor, wherein a plurality of metal nanoparticles are attached to a surface of the nitride based semiconductor, and the surface of the nitride based semiconductor is passivated with at least one thiol compound. The present invention also provides a method of fabricating a nitride-based sensor. The present invention also discloses a porous gallium nitride (GaN) based H2 gas sensor, comprising a GaN based semiconductor with a plurality of Pt nanoparticles attached to a surface, wherein the GaN based semiconductor is passivated with a thiol compound, and wherein the sensor exhibits responsiveness of at least 60% for detection of H2 at a concentration of 30 ppm at room temperature.

7 Claims, 8 Drawing Sheets

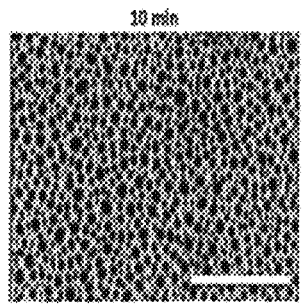
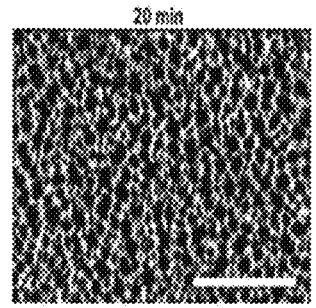
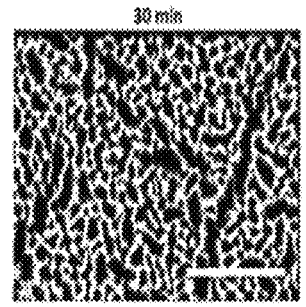
FIG. 1A        FIG. 1B        FIG. 1C
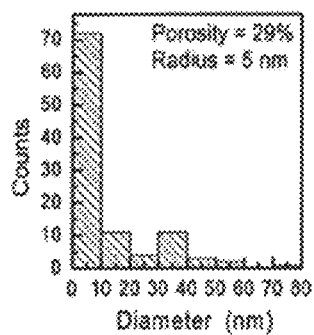
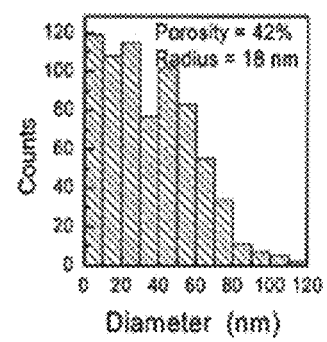
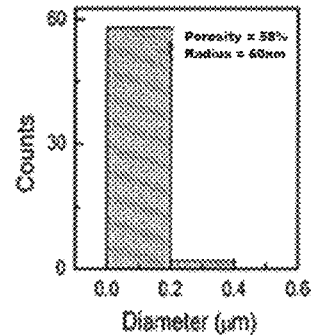
FIG. 1D        FIG. 1E        FIG. 1F

NITRIDE BASED SENSOR

CROSS-REFERENCE TO RELATED APPLICATIONS AND PRIORITY

This patent application is a Divisional of U.S. patent application Ser. No. 16/142,671 filed Sep. 26, 2018. This patent application is herein incorporated by reference in its entirety.

FIELD OF THE INVENTION

The present invention generally relates to a field of gas sensing. Specifically, the present invention relates to a nitride based sensor. Aspects of the present invention also relate to a method of fabricating a nitride based sensor. Further aspects of the present invention provide a porous gallium nitride based $H_2$ gas sensor that exhibits superior responsiveness towards detection of $H_2$ at room temperature.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Porous semiconductors are promising material in comparison to bulk materials as they offer high surface to volume ratio. It enhances their optoelectronic properties, as well as lattice mismatch, and can be handled by controlling their porosity that significantly alters the band gap present in them. Among them, Group III nitrides exhibit high saturation voltage, high thermal stability and wide band gaps ranging from 3.4 eV for GaN up to 6.2 eV for AlN in the case of wurtzite crystal structure.

Recently, GaN micro- and nanostructures, such as porous layers and nanowire arrays, have attracted great researchers because of their distinct properties such as enhanced luminescence, high sensitivity and selectivity in chemical sensing, low dislocation density, relaxing lattice and thermal mismatch-induced strain and suppressing quantum confined stark effect in lnGaN/GaN quantum wells, from a bulk or an epitaxial thin film.

Over the last decade, huge research is being done on gas sensing semiconductors materials such as ZnO and $SnO_2$. Among these gas sensor materials, Group III-nitride is of great importance as they can work in severe climatic conditions such as high/low temperature, high humidity etc. Group III-nitride such as GaN with different morphologies such as porous structures, nanowires, and nanotubes etc. has been synthesized, and are investigated for gas sensing properties. Colloidal graphite grown on GaN substrate has been used as $H_2$ gas sensor, and it demonstrated a limit response to exposure of 100 ppm $H_2/N_2$. Pd/AlGaN/GaN field effect transistor (FET) hetero-structure was used as an $H_2$ gas detector and showed lower limit less than 1 ppm. A sensitivity of 4% is measured from metal composite nanoclusters on GaN nanowires when exposed to 1 ppm $H_2/N_2$ at room temperature.

In last few years, passivation of GaN has been thoroughly explored to handle the issues such as current leakage, carriers trapping in light emitting devices and enhancing the conduction mechanism in high electron mobility transistors. Sulfur-based compounds such as sodium sulfide and ammonium sulfide are mainly used due to their strong bonding with III-V semiconductor; in particular, octadecylthiol (ODT) and thioacetamide (TAM) have been employed to treat GaP, GaN, and GaAs. Nanostructures of GaN, as well as its epitaxial layers, have been passivated with inorganic sulfides to explore the effect of passivation on the gas sensor. However, to the best of knowledge of inventors of the present application, the conventional sensors and methods of detecting gas(es) suffers from a disadvantage that they could not achieve the desired performance characteristics.

There is therefore a need in the art of a gas sensor that can overcome the limitations associated with conventional sensors while exhibiting high sensitivity of gas detection under different temperate conditions. The present invention satisfies the existing needs, inter alia, others and provides $H_2$ gas sensor that is highly sensitive at room temperature.

SUMMARY OF THE INVENTION

Therefore it is an object of the present invention is to provide a nitride based sensor that exhibits superior sensitivity of gas detection under different temperate conditions. Another object of the present invention is to provide a nitride based sensor that exhibits superior responsiveness towards detection of $H_2$ at room temperature. Further, the nitride sensor disclosed in the present invention cost effective.

The present invention generally relates to a field of gas sensing. Specifically, the present invention relates to a nitride based sensor. Aspects of the present invention also relate to a method of fabricating a nitride based sensor. Further aspects of the present invention provide a porous gallium nitride based $H_2$ gas sensor that exhibits superior responsiveness towards detection of $H_2$ at room temperature.

An aspect of the present invention provides a nitride based sensor, said sensor including a nitride based semiconductor, wherein a plurality of metal nanoparticles are attached to a surface of said nitride based semiconductor, and wherein the surface of said nitride based semiconductor is passivated with at least one thiol compound. In an embodiment, the nitride based semiconductor comprises a nitride selected from a group consisting of GaN, AN, AlGaN, InGaN and SiN. In an embodiment, the plurality of metal nanoparticles comprises a metal selected from a group consisting of Pt, Pd, Au, Cu, Ag and alloys selected from a group consisting of from Pt—Pd and Pt—Ag. In an embodiment, the at least one thiol compound is at least one of 1,2-ethanedithiol (EDT) and octadecanethiol (ODT). In an embodiment, the nitride based sensor is capable of sensing gas selected comprising at least one of NO, $NO_2$, $N_2O$, CO and $CO_2$. In an embodiment, the nitride based sensor exhibits porosity of at least 29%. In an embodiment, the nitride based sensor exhibits pores with average radii of at least 5 nm. In an embodiment, the nitride based sensor exhibits responsiveness of at least 60% for detection of $H_2$ at a concentration of 30 ppm at room temperature.

Another aspect of the present invention relates to a method of fabricating a nitride based sensor, said method comprising the steps of: taking a nitride based semiconductor; effecting cleaning of said nitride based semiconductor; effecting deposition of a plurality of metal nanoparticles by sputtering to form metal nanoparticle decorated nitride based semiconductor; effecting etching of said metal nanoparticle decorated nitride based semiconductor; and effecting surface passivation of said etched metal nanoparticle decorated nitride based semiconductor with at least one thiol compound to fabricate the nitride based sensor. In an embodiment, the nitride based semiconductor comprises a nitride selected from a group consisting of GaN, AlN, AlGaN, InGaN and SiN, and wherein said plurality of metal nanoparticles comprises a metal selected from a group consisting of Pt, Pd, Au, Cu, Ag and alloys selected from a group consisting of Pt—Pd and Pt—Ag, further wherein said at least one thiol compound is at least one of 1,2-ethanedithiol (EDT) and octadecanethiol (ODT). In an embodiment, the GaN is in the form of nanostructure comprising pores structures, nanowires or nanoparticles. In an embodiment, the step of cleaning of said nitride based semiconductor comprises effecting sonication of said nitride based semiconductor in each of acetone and 2-propanol for a time period ranging from 2 minutes to 60 minutes. In an embodiment, the method further comprises treatment of the cleaned nitride based semiconductor with nitric acid before effecting the deposition of the plurality of metal nanoparticles. In an embodiment, the step of etching comprises etching of said metal nanoparticle decorated nitride based semiconductor in a solution of $H_2O_2$:HF:$CH_3OH$ with volumetric ratio of 2:1:2 under UV illumination for a time period ranging from 5 minutes to 60 minutes. In an embodiment, the step of surface passivation comprises: treating the etched metal nanoparticle decorated nitride based semiconductor with HF solution to effect removal of oxide from surface of the metal nanoparticles; and treating the HF treated etched metal nanoparticle decorated nitride based semiconductor with at least one thiol compound is at least one of 1,2-ethanedithiol (EDT) and octadecanethiol (ODT) for a time period ranging from 2 minutes to 30 minutes.

Still a further aspect of the present invention provides a porous gallium nitride (GaN) based $H_2$ gas sensor, said sensor comprising a GaN based semiconductor with a plurality of Pt nanoparticles attached to a surface thereof, wherein the GaN based semiconductor is passivated with at least one thiol compound selected from 1,2-ethanedithiol (EDT) and octadecanethiol (ODT), further wherein said sensor exhibits responsiveness of at least 60% for detection of $H_2$ at a concentration of 30 ppm at room temperature.

BRIEF DESCRIPTION OF THE DRAWINGS

The following drawings form part of the present specification and are included to further demonstrate certain aspects of the present invention, the inventions of which can be better understood by reference to one or more of these drawings in combination with the detailed description of specific embodiments presented herein.

FIG. 1A through FIG. 1C illustrates exemplary SEM images depicting morphology of porous GaN surface after carrying out etching for different time period (10, 20 and 30 min respectively), in accordance with the embodiments of the present invention.

FIG. 1D through FIG. 1F illustrates exemplary snippet depicting pore size distribution of porous GaN for different etching time period (10, 20 and 30 min respectively), in accordance with the embodiments of the present invention.

DETAILED DESCRIPTION OF THE INVENTION

Figure 2A:
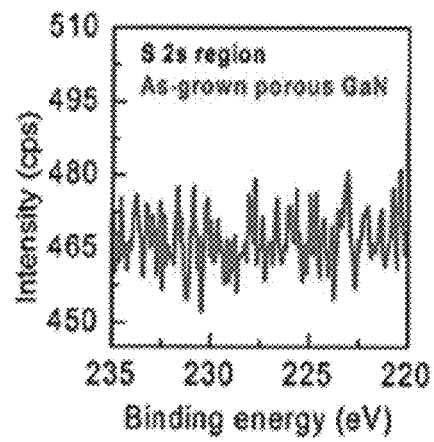
FIG. 2A and FIG. 2B illustrates exemplary XPS spectra of porous GaN and sulfide treated porous GaN for Ga S 2s region, in accordance with the embodiments of the present invention.

The embodiments herein and the various features and advantageous details thereof are explained more comprehensively with reference to the non-limiting embodiments that are detailed in the following description. Descriptions of well-known components and processing techniques are omitted so as to not unnecessarily obscure the embodiments herein. The examples used herein are intended merely to facilitate an understanding of the ways in which the embodiments herein may be practiced and to further enable those of skill in the art to practice the embodiments herein. Accordingly, the examples should not be construed as limiting the scope of the embodiments herein.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

As used in the description herein, the meaning of "a," "an," and "the" includes plural reference unless the context clearly dictates otherwise. Also, as used in the description herein, the meaning of "in" includes "in" and "on" unless the context clearly dictates otherwise.

As used herein, the terms "comprise", "comprises", "comprising", "include", "includes", and "including" are meant to be non-limiting, i.e., other steps and other ingredients which do not affect the end of result can be added. The above terms encompass the terms "consisting of" and "consisting essentially of".

As used herein, the terms "composition" "blend," or "mixture" are all intended to be used interchangeably.

As used herein, the term "room temperature" denotes the temperature ranging from 30° C. to 40° C.

The terms "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The present invention generally relates to a field of gas sensing. Specifically, the present invention relates to a nitride based sensor. Aspects of the present invention also relates to a method of fabricating a nitride based sensor. Further aspects of the present invention provide a porous gallium nitride based $H_2$ gas sensor that exhibits superior responsiveness towards detection of $H_2$ at room temperature.

An aspect of the present invention provides a nitride based sensor, said sensor comprising a nitride based semiconductor, wherein a plurality of metal nanoparticles are attached to a surface of said nitride based semiconductor, and wherein the surface of said nitride based semiconductor is passivated with at least one thiol compound.

In an embodiment, the nitride based semiconductor comprises a nitride selected from a group consisting of GaN, AN, AlGaN, InGaN and SiN. In an embodiment, the nitride based sensor is adapted for sensing gas selected comprising at least one of NO, $NO_2$, $N_2O$, CO and $CO_2$. In an embodiment, the nitride based semiconductor comprises GaN based semiconductor. However, a person skilled in the art should appreciate that any other nitride based semiconductor can be utilized to sub-serve its intended purpose as laid down in embodiments of the present invention without departing from the scope and spirit of the present invention.

In an embodiment, the plurality of metal nanoparticles comprises a metal selected from a group consisting of Pt, Pd, Au, Cu, Ag and alloys selected from a group consisting of Pt—Pd and Pt—Ag. In an embodiment, the plurality of metal nanoparticles comprises Pt metal. However, it should be appreciated that nanoparticles of any other metal, as known to or appreciated by a person skilled in the art, can be deposited to sub-serve its intended purpose as laid down in embodiments of the present invention without departing from the scope and spirit of the present invention.

In an embodiment, the at least one thiol compound is selected from any one of 1,2-ethanedithiol (EDT) and octadecanethiol (ODT). However, utilization of any other thiol compound, as known to a person skilled in the art, is completely within the scope of the present invention. In an embodiment, the nitride based sensor exhibits porosity of at least 29%. Preferably, the nitride based sensor exhibits porosity of at least 40%, more preferably, the nitride based sensor exhibits porosity of at least 50%, and most preferably, the nitride based sensor exhibits porosity of at least 55%. In an embodiment, the nitride based sensor exhibits pores with average radii of at least 5 nm. Preferably, the nitride based sensor exhibits pores with average radii of at least 10 nm, more preferably, the nitride based sensor exhibits pores with average radii of at least 20 nm and most preferably, the nitride based sensor exhibits pores with average radii of at least 50 nm. In an embodiment, the nitride based sensor exhibits responsiveness of at least 60% for detection of $H_2$ at a concentration of 30 ppm at room temperature.

Another aspect of the present invention relates to a method of fabricating a nitride based sensor, said method comprising the steps of: taking a nitride based semiconductor; effecting cleaning of said nitride based semiconductor; effecting deposition of a plurality of metal nanoparticles by sputtering to form metal nanoparticle decorated nitride based semiconductor; effecting etching of said metal nanoparticle decorated nitride based semiconductor; and effecting surface passivation of said etched metal nanoparticle decorated nitride based semiconductor with at least one thiol compound to fabricate the nitride based sensor. In an embodiment, the nitride based semiconductor comprises a nitride selected from a group consisting of GaN, AN, AlGaN, InGaN and SiN. In an embodiment, the GaN is in the form of a nanostructure comprising pores structures, nanowires or nanoparticles. In an embodiment, the plurality of metal nanoparticles comprises a metal selected from a group consisting of Pt, Pd, Au, Cu, Ag and alloys selected from a group consisting of Pt—Pd and Pt—Ag. In an embodiment, the at least one thiol compound is selected from at least one of 1,2-ethanedithiol (EDT) and octadecanethiol (ODT).

In an embodiment, the step of cleaning of said nitride based semiconductor comprises effecting sonication of said nitride based semiconductor in each of acetone and 2-propanol for a time period ranging from 2 minutes to 60 minutes, preferably, for a time period ranging from 2 minutes to 30 minutes and most preferably, for a time period ranging from 2 minutes to 15 minutes.

In an embodiment, the method further comprises treatment of the cleaned nitride based semiconductor with nitric acid before effecting the deposition of the plurality of metal nanoparticles. In an embodiment, the step of etching comprises etching of said metal nanoparticle decorated nitride based semiconductor in a solution of $H_2O_2$:HF:$CH_3OH$ with volumetric ratio of 2:1:2 under UV illumination for a time period ranging from 5 minutes to 60 minutes, preferably, for a time period ranging from 5 minutes to 40 minutes, and most preferably, for a time period ranging from 10 minutes to 30 minutes. In an embodiment, the step of surface passivation comprises: treating the etched metal nanoparticle decorated nitride based semiconductor with HF solution to effect removal of oxide from surface of the metal nanoparticles; and treating the HF treated etched metal nanoparticle decorated nitride based semiconductor with at least one thiol compound selected from 1,2-ethanedithiol (EDT) and octadecanethiol (ODT) for a time period ranging from 2 minutes to 30 minutes, preferably, for a time period ranging from 3 minutes to 20 minutes, and most preferably, for about 5 minutes.

Still further aspect of the present invention provides a porous gallium nitride based $H_2$ gas sensor, said sensor comprising a GaN based semiconductor with a plurality of Pt nanoparticles attached to a surface thereof, wherein the GaN based semiconductor is passivated with at least one thiol compound selected from 1,2-ethanedithiol (EDT) and octadecanethiol (ODT), further wherein said sensor exhibits responsiveness of at least 60% for detection of $H_2$ at a concentration of 30 ppm at room temperature.

Examples

Pre-Treatment of GaN Film

For the preparation of platinum (Pt)-decorated porous GaN based sensor, a doped n-type GaN was used. The doped GaN was grown on a c-axis (0001) sapphire substrate having a resistivity less than 0.05 Ω·cm. The film was purchased from Xiamen Powerway Advanced Material Co. Ltd. The GaN film has a thickness of about 30 µm with a carrier concentration of about $3.4 \times 10^{17}$ cm$^{-3}$. The film was cleaned by sonication in acetone for about 5 min, followed by its sonication in 2-propanol for about 5 min. Thereafter, it was immersed in HNO3 at 65° C. for about 15 min, rinsed with distilled water and methanol.

Preparation of Platinum (Pt) Decorated Porous GaN Sensor

Two narrow stripes of Pt having a thickness of about 10 nm separated by few millimeter was deposited on the above prepared GaN film by sputtering. Later, it was etched by a metal-assisted electroless etching process in a solvent mixture (solution) of $H_2O_2$, HF and $CH_3OH$ in a volumetric ratio of 2:1:2, under UV illumination for different time period (etching was carried for about 10, 20 and 30 minutes) to effect porosity and generation of Pt nanostructures/nanoparticles. Thereafter, Platinum (Pt) decorated porous GaN structure was removed from the solvent mixture, rinsed with distilled water and dipped in about 49% HF to remove any oxide present on the surface of the nanostructures, followed by its immersion in 1,2-ethanedithiol (EDT) for about 5 minutes, rinsed with ethanol and dried under $N_2$. Pt nanoparticles with 5-nm radii were then deposited on the surface of the porous GaN layer using ultra high vacuum chamber for nanoparticles production system from Mantis Deposition Ltd. The electrode contact was deposited by sputtering and is formed of about 8 nm NiCr layer followed by a 25 nm Au layer.

Morphology of Porous GaN Surface After Etching Process

FIG. 1A through FIG. 1C illustrate exemplary SEM images depicting morphology of porous GaN surface after carrying out etching for different time periods (10, 20 and 30 min respectively), in accordance with embodiments of the present invention. The porosity and the pore size distribution were determined for different etching time periods using image-J software. As can be seen in FIG. 1A, for a short etching period of about 10 minutes, pores are circular in shape with an average diameter of about 10 nm and porosity of about 29%. With increases in etching time up to 20 minutes, the pores collapsed with the nearby pores and become larger (circular in shape) in size with average diameter ranges up to 36 nm having a porosity of about 42% as visible in FIG. 1B. FIG. 1C illustrates the exemplary SEM images showing an increase in pores collapsing and formation of much large size pores (average size of about 120 nm) with porosity of about 58%, when the etching time was increased to about 30 minutes. FIG. 1D through FIG. 1F illustrate exemplary snippets depicting pore size distribution of porous GaN for different etching time period (10, 20 and 30 min respectively), in accordance with the embodiments of the present invention.

Effect of Sulfur Treatment on Porous GaN

Figure 2B:
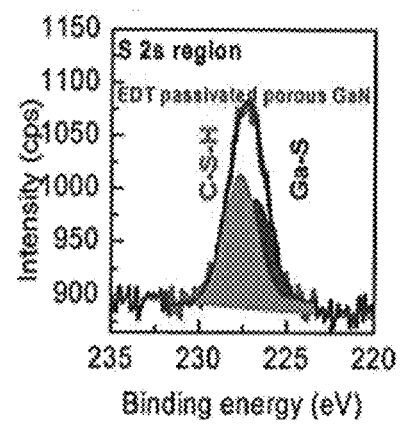
Figure 2C:
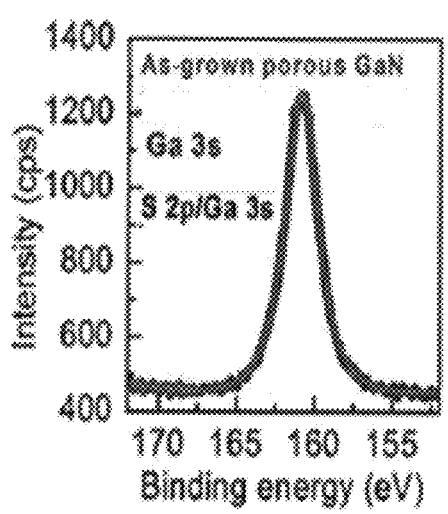
FIG. 2C and FIG. 2D illustrates exemplary XPS spectra of porous GaN and sulfide treated porous GaN for Ga 3s/S 2p region, in accordance with the embodiments of the present invention.
Figure 2D:
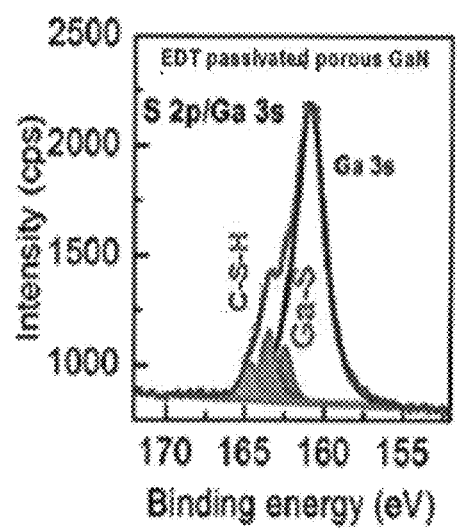

To measure change in chemical properties of porous GaN before and after treatment (surface passivation) with sulfur (thiol compound), an X-ray photoelectron spectroscopy (XPS) measurement was conducted on porous GaN and sulfur-treated porous GaN. FIG. 2A and FIG. 2B illustrates exemplary XPS spectra of porous GaN and sulfide treated porous GaN for Ga S 2s region, in accordance with the embodiments of the present invention. As can be seen a FIG. 2B a clear peak at ~227.3 eV emerged that confirmed the presence of sulfur in porous GaN. The S 2s core level was fitted with two peaks located at 226.7 eV and 227.7 eV corresponding to Ga—S and C—S—H bonds, respectively. FIG. 2C and FIG. 2D illustrates exemplary XPS spectra of porous GaN and sulfide treated porous GaN for Ga 3s/S 2p region, in accordance with the embodiments of the present invention. As can be seen in FIG. 2C and FIG. 2D, a comparison of Ga 3s/S 2p region for as-grown porous GaN and 1,2-ethanedithiol (EDT) passivated porous GaN was demonstrated. A clear peak around 163.4 eV emerged in the treated sample that confirmed the presence of sulfur. The additional S 2p contribution was fitted using two (S $2p_{3/2}$, S $2p_{1/2}$) doublets. The S $2p_{3/2}$ components located at 162.5 eV and 163.4 eV corresponds to Ga—S—C and C—S—H bonds, respectively. It is worth noting that the usual peak at ~168 eV corresponding to S—O is not present, indicating that trace amount of S—O is beyond the detection limit, as the sample were loaded into the XPS ultrahigh vacuum chamber right after preparation, thus, reducing the effect of S oxidation. After the sulfur treatment, the electrical contacts were deposited on the top of porous GaN and the gas sensors were tested for $H_2$ gas detection.

Figure 3A:
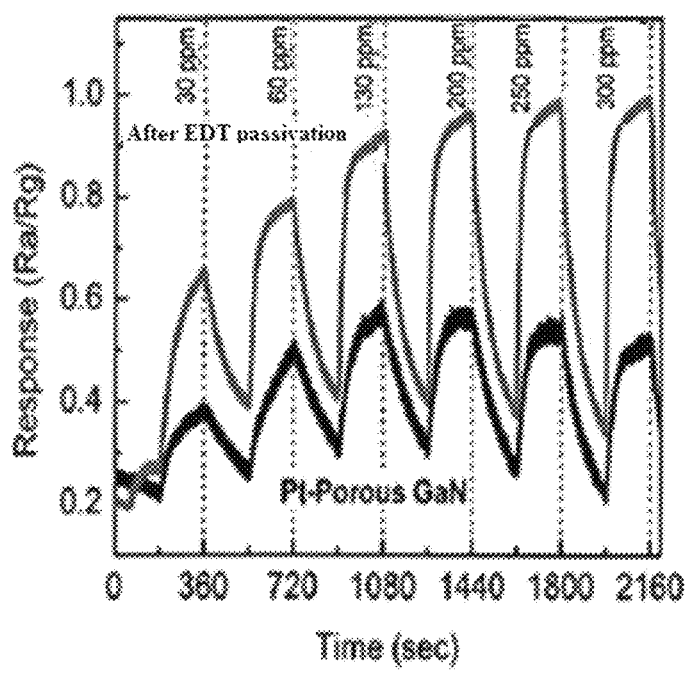
FIG. 3A illustrates an exemplary graph depicting response of Pt-porous GaN structure with and without sulfide treatment at room temperature in $H_2$ gas detection as a function of time, in accordance with the embodiments of the present invention.
Figure 3B:
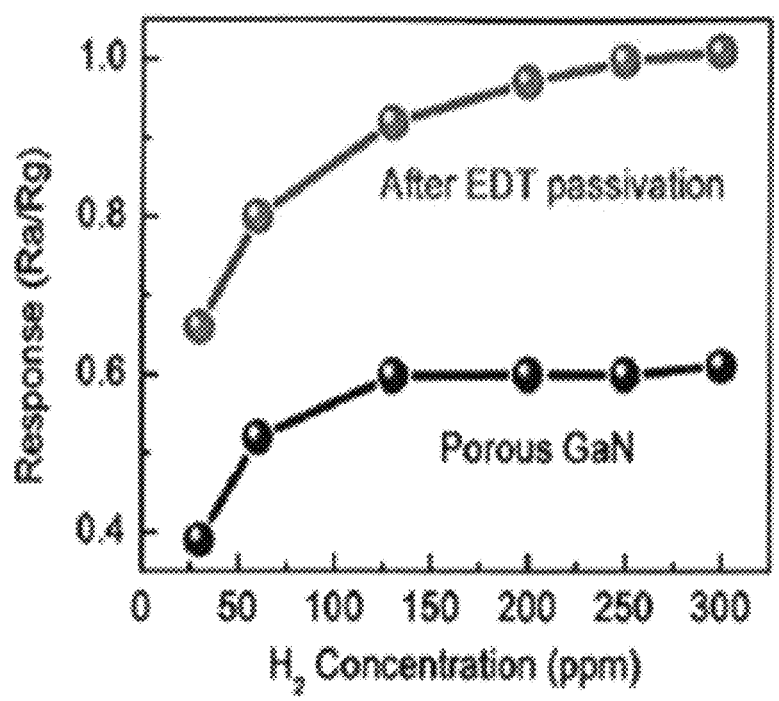
FIG. 3B illustrates an exemplary graph depicting response of Pt-porous GaN structure with and without sulfide treatment at room temperature in $H_2$ gas detection as a function of $H_2$ gas concentration, in accordance with the embodiments of the present invention.

FIG. 3A illustrates an exemplary graph depicting response of Pt-porous GaN structure with and without sulfide treatment at room temperature in $H_2$ gas detection as a function of time, in accordance with the embodiments of the present invention. FIG. 3A demonstrate the response of the Pt-porous GaN gas sensor with porosity equal to 58% before and after sulfur treatment at room temperature. It was found that prior to passivation, the sensitivity of the sensor varies from 40% to 59% with varying $H_2$ concentration ranging from 30 to 300 ppm and the same response can be repeatedly observed. However, on treatment with sulfur, sensor response increased to about 65% for $H_2$ gas concentration equal to about 30 ppm. This increase of response for lower $H_2$ concentration is due to the presence of sulfur. FIG. 3B illustrates an exemplary graph depicting response of Pt-porous GaN structure with and without sulfide treatment at room temperature in $H_2$ gas detection as a function of $H_2$ gas concentration, in accordance with the embodiments of the present invention. As can be seen in FIG. 3B, on increasing $H_2$ concentration, untreated gas sensor (without sulfur treatment) showed saturation at a concentration of about 130 ppm. The observed saturation may be attributed to a saturation of the adsorbed $H_2$ atoms at the porous surface, resulting in the whole coverage of the porous surface area, which may block further adsorption and interaction of $H_2$ atoms with the sensing surface. However, for sulfur treated sensor response is significantly high with increase in $H_2$ concentration. Hence, treatment with sulfur drastically improves the performance of $H_2$ gas sensor at room temperature.

Figure 4:
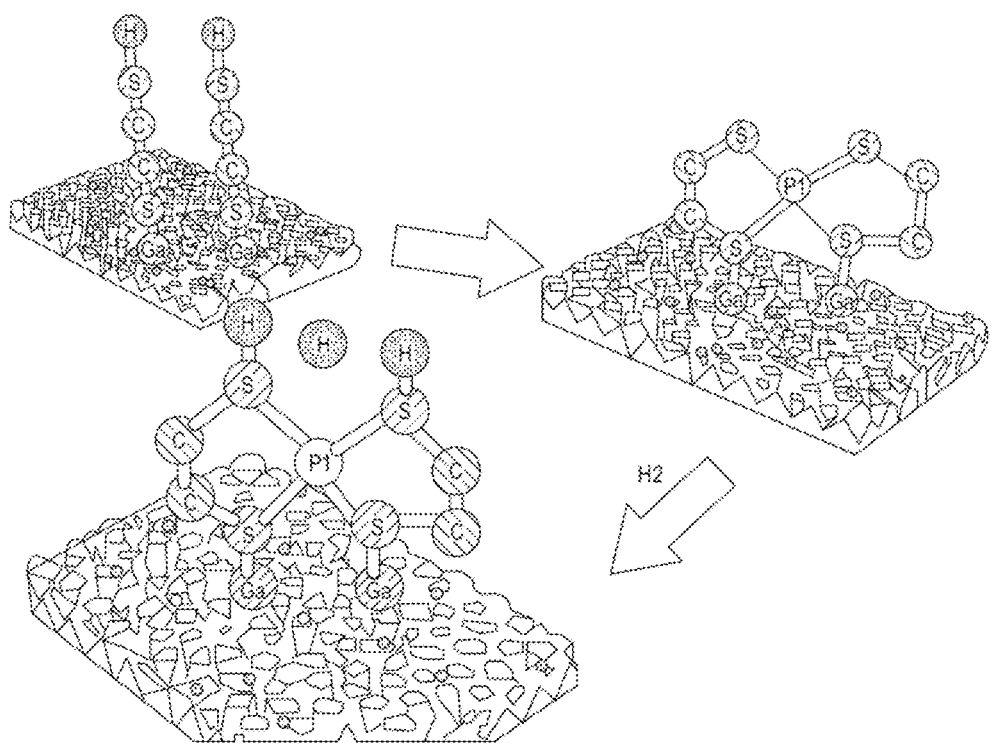
FIG. 4 illustrates an exemplary snippet depicting schematic diagram of the $H_2$ sensing mechanism of sulfur treated Pt-porous GaN sensor, in accordance with the embodiments of the present invention.

FIG. 4 illustrates an exemplary snippet depicting $H_2$ sensing mechanism of sulphur treated Pt-porous GaN sensor, in accordance with the embodiments of the present invention. The presence of sulfur on porous GaN sufficiently enhances the sensitivity of Pt porous GaN sensor. Sulfur effectively removes the defects present on the surface of porous GaN by forming gallium ethanedithiolates complex, and hence, improves the surface stability. Further, presence of Pt nanoparticles on the surface enables two nearest gallium ethanedithiolates to make dangling bond and a sulfide atom get connected to hydrogen atom. When an $H_2$ gas was brought near to the surface of the sensor, it dissociated and the hydrogen gets fixed on the sulfide atom. This results in improvement in the electrical response of the gas sensor due to reduction of charge recombination rates and enhancement in the charge extraction.

Figure 5A:
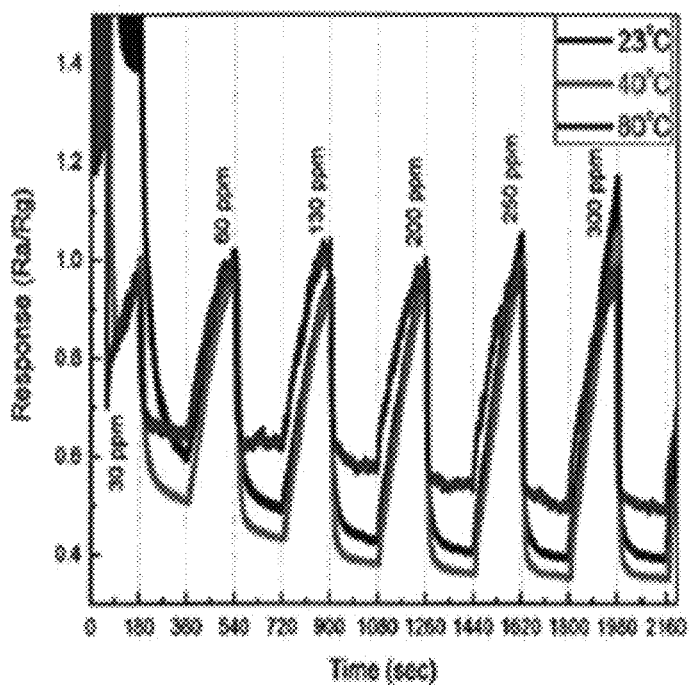
FIG. 5A illustrates an exemplary graph depicting response of a sulphide treated Pt-porous GaN gas sensor having a porosity of about 58% in $H_2$ gas detection at different temperatures (23° C., 40° C. and 80° C. respectively) over a period of time, in accordance with the embodiments of the present invention.

FIG. 5A illustrates an exemplary graph depicting response of a sulphide treated Pt-porous GaN gas sensor having a porosity of about 58% in $H_2$ gas detection at different temperatures (23° C., 40° C. and 80° C. respectively) over a period of time, in accordance with the embodiments of the present invention. As can be seen in FIG. 5A, the effect of temperatures on sensitivity for 1,2-ethanedithiol (EDT) treated Pt-porous GaN sensor with porosity equal to 58% at 60 ppm of $H_2$ gas concentration was demonstrated. The performance of the sensor was investigated at 23° C., 60° C., and 80° C. respectively. FIG. 5A shows that the responses of the sensor at 80° C. were high as compared to responses at 23° C. as thermal energy at higher temperature was sufficient enough to overcome the activation energy barrier of the chemical reaction occurred between sulfur (S) and disassociation of $H_2$ gas molecules. When the working temperature of the sensor increases up to 80° C., the sensor response to 30-300 ppm of $H_2$ is approximately twofold higher compared to when worked at room temperature. Other parameters limiting gas sensing characteristics of porous semiconducting nanostructures are mainly the surface-to-volume ratio and surface morphology. These results clearly demonstrate that the enhancement of response becomes more evident at higher temperatures.

Figure 5B:
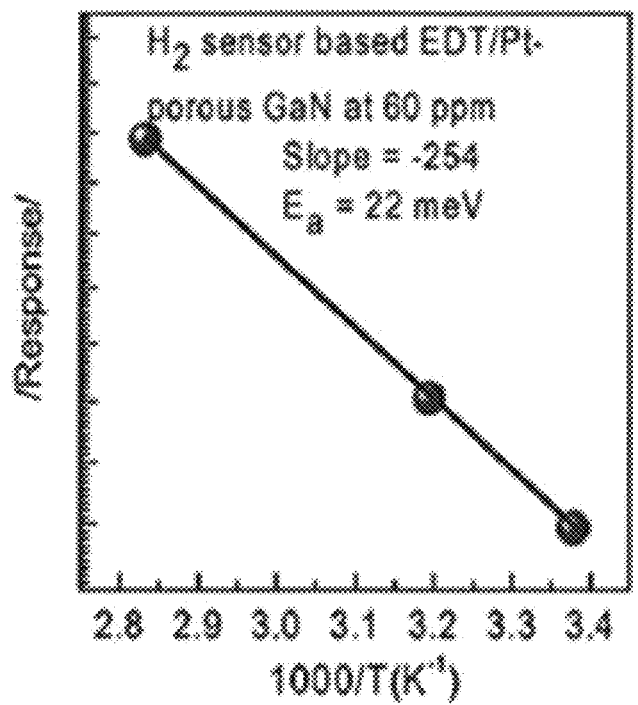
FIG. 5B illustrates an exemplary graph depicting response of a sulphide treated Pt-porous GaN gas sensor at a given temperature for a $H_2$ gas concentration of about 60 ppm, in accordance with the embodiments of the present invention.

FIG. 5B illustrates an exemplary graph depicting response of a sulphide (thiol compound) treated Pt-porous GaN gas sensor at a given temperature for a $H_2$ gas concentration of about 60 ppm, in accordance with the embodiments of the present invention. The conductivity of n-type semiconductor at room temperature is expressed by the following relationship:

$$\sigma = \sigma_0 \exp(-E_a/(k_B T))$$

where $\sigma$ is the electrical conductivity; $E_a$ is the activation energy; $k_B$ is the Boltzmann constant, and T is the room temperature in Kelvin. By plotting the logarithm of the response versus 1/T as shown in FIG. 5B, the activation energy of the 1,2-ethanedithiol (EDT)/Pt porous GaN sensor was calculated from the slope of the Arrhenius plot and was found to be about 22 meV. The observed value was much smaller as compared to the activation energy value of 25 meV and 29.4 meV obtained for GaN nanowires and GaN nanotubes. This small activation energy on sulfur treatment confirmed that the sulphide-treated Pt-porous GaN sensor have high sensitivity and quick response. Further, etching for three different time period effects generation of three different porous GaN having porosity of about 29%, 42%, and 58%. This increase in the porosity of porous GaN strongly influenced the sensitivity of the sensor.

Figure 6:
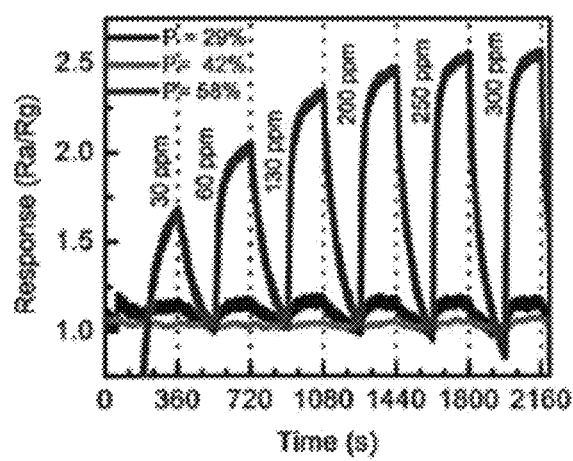
FIG. 6 illustrates an exemplary graph depicting variation in response of a sulphide treated Pt-porous GaN gas sensor as a function of porosity (29%, 42% and 58% respectively) over a period of time, in accordance with the embodiments of the present invention.

FIG. 6 illustrates an exemplary graph depicting variation in response of a sulphide treated Pt-porous GaN gas sensor as a function of porosity (29%, 42% and 58% respectively) over a period of time, in accordance with the embodiments of the present invention. As can be seen in FIG. 6, response of sulphide-treated Pt-porous GaN sensors with different porosity i.e. 29%, 42%, and 58% was plotted against time at room temperature. It could be observed that the response of sensor towards $H_2$ increases with increase in porosity of GaN. As visible in FIG. 6, for GaN sensor with porosity of 58%, response towards $H_2$ gas detection enhanced drastically.

Figure 7:
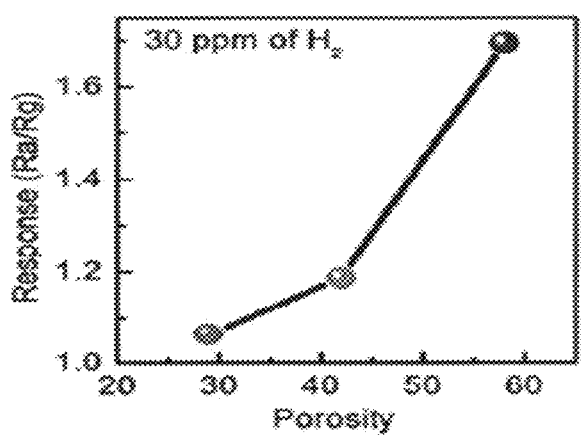
FIG. 7 illustrates an exemplary graph depicting variation in response of a sulphide treated Pt-porous GaN gas sensor as a function of porosity for a $H_2$ gas concentration of about 30 ppm, in accordance with the embodiments of the present invention.

FIG. 7 illustrates an exemplary graph depicting variation in response of a sulphide treated Pt-porous GaN gas sensor as a function of porosity for a $H_2$ gas concentration of about 30 ppm, in accordance with the embodiments of the present invention. As can be seen in FIG. 7, at 30 ppm of $H_2$ gas, with increase in pore radius (i.e. increasing the porosity), the 1,2-ethanedithiol (EDT)/Pt-porous GaN will have larger exposure area that resulted in higher response of gas sensor towards $H_2$ gas detection. The diffusion rate of an $H_2$ gas is very high for bigger pores size on the upper layer of thin film. To facilitate the porosity outcomes measured experimentally from sulphide-treated Pt-porous GaN gas sensors, the influence of $H_2$ gas transport on the sensitivity of the porous GaN were investigated theoretically. The mechanism of gas diffusion through a porous material depends on the size of the pores, surface diffusion, and Knudsen diffusion. Knudsen diffusion coefficient ($D_K$) is given by equation (1) for a mesoporous film.

$$D_K = \frac{4r}{3}\sqrt{\frac{2RT}{\pi M}} \qquad (1)$$

where T is the temperature, r is the pore radius, R is gas constant, and M is molecular weight of the $H_2$ diffusing gas. To simulate the $H_2$ concentration inside the porous GaN layer depending on the pore size, we have used the diffusion equations (2), which depend on gas concentration in a mesoporous layer given by the gas diffusion rate and the surface reaction rate.

$$\frac{\partial C}{\partial t} = D_k \frac{\partial^2 C}{\partial x^2} - KC \qquad (2)$$

where C is the concentration of $H_2$, t is the time, x is the depth from the surface of the porous GaN, $D_k$ is the diffusion coefficient, and K is the rate constant of the surface reaction. By solving the equation at the steady-state condition ($\partial C_A/\partial t = 0$), the following gas concentration profile can be obtained:

$$C = C_S \frac{\cosh\left(1 - \frac{x}{L}\right)m}{\cosh(m)}, \; m = L\sqrt{K/D_k} \qquad (3)$$

where $C_s$ is the concentration of $H_2$ gas at the surface and L is porous layer thickness. The diffusion coefficient depends on the pore radius, so the gas concentration profile is also dependent on pore size if K is constant.

Figure 8A:
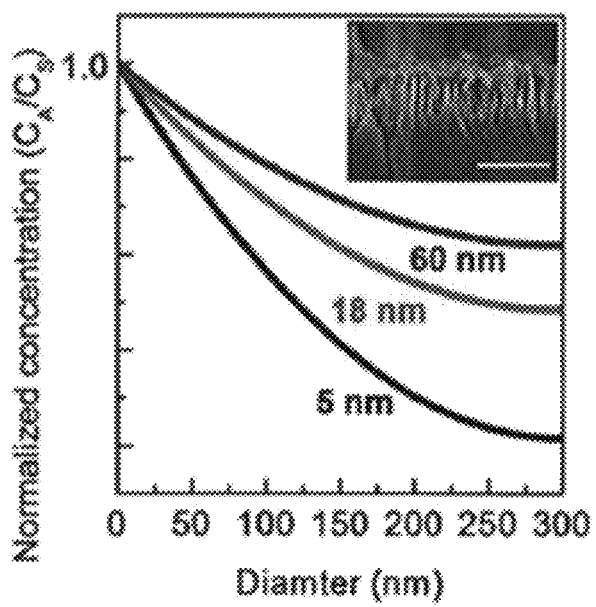
FIG. 8A illustrates an exemplary graph depicting variation of simulated $H_2$ gas concentration profile inside porous GaN layer with different values of $\sqrt{k/Dk}$ corresponding to different pore sizes (5, 18, and 60 nm) as a function of film thickness, in accordance with the embodiments of the present invention.
Figure 8B:
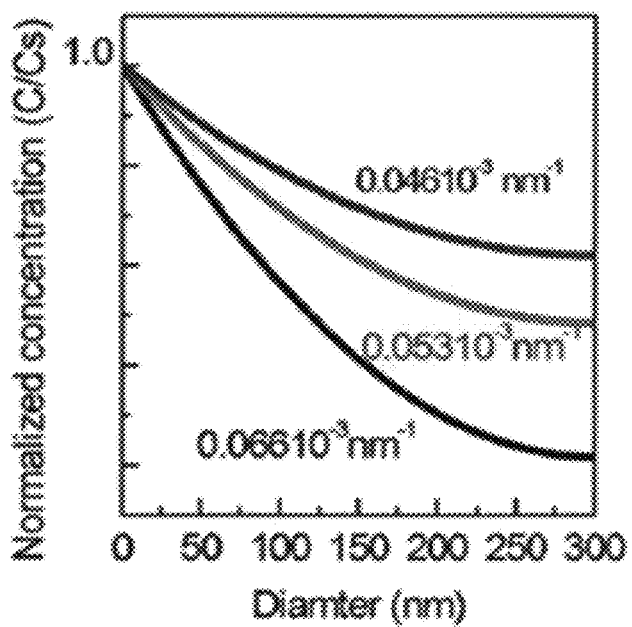
FIG. 8B illustrates an exemplary graph depicting variation of simulated $H_2$ concentration profile inside porous GaN layer with different values of $\sqrt{k/Dk}$ corresponding to different pore sizes (5, 18, and 60 nm) as a function of surface concentration, in accordance with the embodiments of the present invention.

FIG. 8A illustrates an exemplary graph depicting variation of simulated $H_2$ gas concentration profile inside porous GaN layer with different values of $\sqrt{k/Dk}$ corresponding to different pore sizes (5, 18, and 60 nm) as a function of film thickness, in accordance with the embodiments of the present invention. FIG. 8B illustrates an exemplary graph depicting variation of simulated $H_2$ concentration profile inside porous GaN layer with different values of $\sqrt{k/Dk}$ corresponding to different pore sizes (5, 18, and 60 nm) as a function of surface concentration, in accordance with the embodiments of the present invention. FIG. 8A and FIG. 8B show the gas concentration profiles simulated from equation (3) for a porous GaN layer of thickness around 300 nm in the inset at various pore size (5 nm, 18 nm, and 60 nm) and K=100000 s$^{-1}$. The profiles changes with variation in $\sqrt{K/D_k}$. The gas concentration decreases as $H_2$ diffuses toward the bottom of porous GaN, depending on pore size. For larger pore size equal to 60 nm, the concentration difference between the surface and the bottom is very small. However, when the pores size decreases to 5 nm, this concentration difference rises i.e. most of the $H_2$ gas cannot reached to the bottom of the porous GaN when the layer is dense. Thus, region of porous GaN where $H_2$ gas cannot reach does not contribute to the sensor response. It can be expected from the simulation result that increasing the pore size likely increases the $H_2$ concentration in the total volume of porous film, thus, increasing the sensor response. These simulation results clearly explained the results visible in FIG. 8B, which demonstrate the relation between pore size and normalized concentration for different diffusion coefficient $D_k$.

The gas concentration in the porous GaN is not constant and it decreases with increasing diffusion depth due to the surface reaction. It was assumed that there was a uniform stack of infinitesimal thin sheets with electric conductance $\sigma(x)$. The conductance of the porous layer is given by the integral of $\sigma(x)$ between x=0 and L. The conductance $\sigma(x)$ is defined as the product of conductance in air $\sigma_0$ and sensitivity constants presented by the following equation (4).

$$\sigma(x) = \sigma_0(1 + aC_A) \quad (4)$$

where a and $C_A$ are the sensitivity constants. As the resistance is the inverse of conductance, integration of $1/\sigma(x)$ from the surface (x=0) to the bottom of the porous GaN (x=L) gives the total resistance of the sensing layer. The sensor response (S) can be obtained by the total resistance in $H_2$ gas and in air, as expressed in equation (5).

$$S = \frac{Ra}{Rg} = 1 + \alpha C_S \frac{\tanh(m)}{m}, \; m = L\sqrt{K/D_k} \quad (5)$$

Figure 9A:
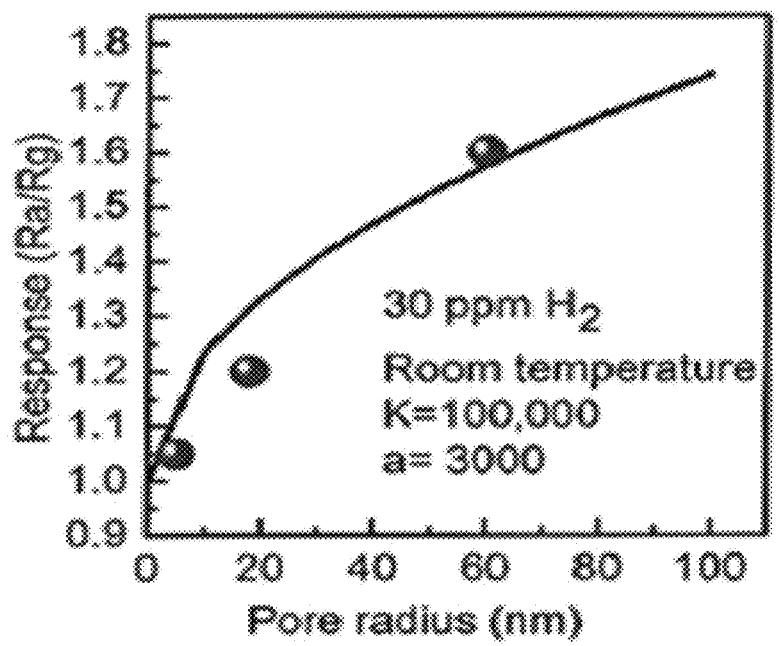
FIG. 9A and FIG. 9B illustrates an exemplary graph depicting response of a simulated and experimental sensor for a $H_2$ gas concentration of 30 ppm and 200 ppm at room temperature as a function of pore radius of the porous sensing layer, in accordance with the embodiments of the present invention.
Figure 9B:
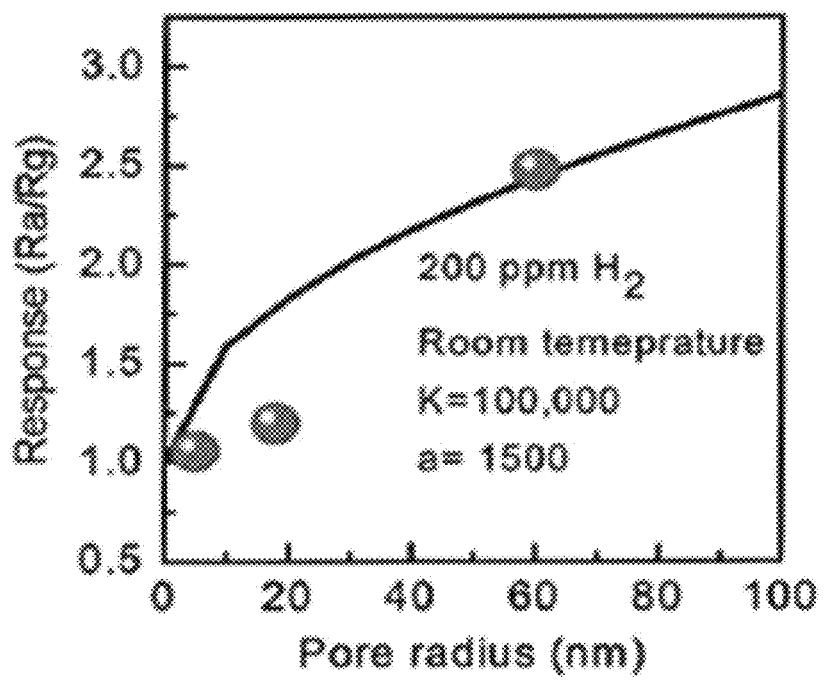

The response or responsiveness (sensitivity towards detection of gas) of the sensor, S, is the ratio of $R_a$ to $R_g$. FIG. 9A and FIG. 9B illustrates an exemplary graph depicting response of a simulated (represented by dark line) and experimental (represented by circle) sensor for a $H_2$ gas concentration of 30 ppm and 200 ppm at room temperature as a function of pore radius of the porous sensing layer, in accordance with the embodiments of the present invention. The experimental results (represented by circle) were also plotted in FIG. 9A and FIG. 9B, for both of the $H_2$ concentrations (30 ppm and 200 ppm). The graphs showed good agreement between the experimental data obtained on porous GaN layer with 300 mm thickness and the theoretical data. The agreement between experimental data and theoretical data revealed that increase in film pore size enhanced the response of the sensor towards $H_2$ gas. It was also noted that the sensor response to $H_2$ gas doesn't show saturation as seen in the theoretical data curve.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A method of fabricating a porous nitride based $H_2$ gas sensor, said method comprising the steps of:
   cleaning a nitride based semiconductor;
   depositing a plurality of metal nanoparticles by sputtering onto the nitride based semiconductor to form a metal nanoparticle decorated nitride based semiconductor;
   etching said metal nanoparticle decorated nitride based semiconductor; and
   applying surface passivation to said etched metal nanoparticle decorated nitride based semiconductor with at least one thiol compound to fabricate the porous nitride based $H_2$ gas sensor,
   wherein said at least one thiol compound is at least one of 1,2-ethanedithiol (EDT) and octadecanethiol (ODT), and
   wherein said porous nitride based $H_2$ gas sensor exhibits porosity of at least 29%.

2. The method as claimed in claim 1, wherein said nitride based semiconductor comprises a nitride selected from a group consisting of GaN, AN, AlGaN, InGaN and SiN and wherein said plurality of metal nanoparticles comprises a metal selected from a group consisting of Pt, Pd, Au, Cu, Ag and alloys selected from Pt—Pd and Pt—Ag.

3. The method as claimed in claim 2, wherein the GaN is in the form of a nanostructure comprising pores structures, nanowires or nanoparticles.

4. The method as claimed in claim 1, wherein the step of cleaning of said nitride based semiconductor comprises sonication of said nitride based semiconductor in each of acetone and 2-propanol for a time period ranging from 2 minutes to 60 minutes.

5. The method as claimed in claim 1, wherein the method further comprises treatment of the cleaned nitride based semiconductor with nitric acid before depositing the plurality of metal nanoparticles.

6. The method as claimed in claim 1, wherein the step of etching comprises etching of said metal nanoparticle decorated nitride based semiconductor in a solution of $H_2O_2$:HF:$CH_3OH$ with volumetric ratio of 2:1:2 under UV illumination for a time period ranging from 5 minutes to 60 minutes.

7. The method as claimed in claim 1, wherein the step of surface passivation comprises:
   treating the etched metal nanoparticle decorated nitride based semiconductor with HF solution to effect removal of oxide from surface of the metal nanoparticles; and
   treating the HF treated etched metal nanoparticle decorated nitride based semiconductor with at least one thiol compound selected from 1,2-ethanedithiol (EDT) and octadecanethiol (ODT) for a time period ranging from 2 minutes to 30 minutes.

* * * * *